US012207956B2

(12) United States Patent
Giebel et al.

(10) Patent No.: US 12,207,956 B2
(45) Date of Patent: Jan. 28, 2025

(54) COMPUTED TOMOGRAPHY DEVICE HAVING A RADIATION PROTECTION APPARATUS FOR COVERING AN OPENING OF A GANTRY

(71) Applicant: Siemens Healthineers AG, Forchheim (DE)

(72) Inventors: Steffen Giebel, Wiesenthau (DE); Jens Fehre, Hausen (DE); Marco Koehler, Adelsdorf (DE); Hans-Juergen Mueller, Pretzfeld (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 255 days.

(21) Appl. No.: 17/948,354

(22) Filed: Sep. 20, 2022

(65) Prior Publication Data
US 2023/0094920 A1 Mar. 30, 2023

(30) Foreign Application Priority Data
Sep. 24, 2021 (DE) ..................... 10 2021 210 677.3

(51) Int. Cl.
*A61B 6/03* (2006.01)
*A61B 6/00* (2006.01)
(Continued)

(52) U.S. Cl.
CPC ............. *A61B 6/035* (2013.01); *A61B 6/107* (2013.01); *A61B 6/4405* (2013.01); *A61B 6/4435* (2013.01); *A61B 6/501* (2013.01)

(58) Field of Classification Search
CPC .......... A61B 6/03; A61B 6/032; A61B 6/035; A61B 6/04; A61B 6/0407; A61B 6/0442;
(Continued)

(56) References Cited

U.S. PATENT DOCUMENTS 5,937,028 A * 8/1999 Tybinkowski ....... G01N 23/046
378/4
7,099,427 B2 * 8/2006 Cadwalader ........... A61B 6/107
250/519.1
(Continued)

FOREIGN PATENT DOCUMENTS

CN 208693304 U 4/2019
DE 102020206784 A1 7/2021
WO WO 2014119001 A1 8/2014

*Primary Examiner* — Allen C. Ho
(74) *Attorney, Agent, or Firm* — Harness, Dickey & Pierce, P.L.C.

(57) ABSTRACT

The computed tomography device has a gantry with an opening and a radiation protection apparatus for covering the opening. The radiation protection apparatus includes a radiation protection cover and a pivoting apparatus, wherein an object under examination may be inserted into the opening along a system axis of the gantry when the radiation protection cover is in a first position relative to the gantry. The radiation protection cover is pivotably mounted relative to the gantry about a pivot axis by the pivoting apparatus such that a first pivoting motion of the radiation protection cover about the pivot axis enables the radiation protection cover to be lowered relative to the gantry from the first position to a second position. The computed tomography device may furthermore include at least one of a lighting system or a camera system.

20 Claims, 3 Drawing Sheets

(51) Int. Cl.
*A61B 6/10* (2006.01)
*A61B 6/50* (2024.01)

(58) Field of Classification Search
CPC ......... A61B 6/107; A61B 6/44; A61B 6/4405; A61B 6/4411; A61B 6/4423; A61B 6/4429; A61B 6/4435; A61B 6/501; A61B 6/037; A61B 6/4447; A61B 6/502; A61B 6/508
USPC ....................... 378/4, 20, 203, 204, 207–209
See application file for complete search history.

(56) References Cited

U.S. PATENT DOCUMENTS

| | | | | |
|---|---|---|---|---|
| 7,175,347 B2* | 2/2007 | Tybinkowski | ....... | A61B 6/4488 378/198 |
| 7,384,194 B2* | 6/2008 | Gatten | ................. | G01N 23/046 378/57 |
| 7,492,858 B2* | 2/2009 | Partain | ................... | A61B 6/502 378/37 |
| 7,593,503 B2* | 9/2009 | Sukovic | ................. | A61B 6/107 378/4 |
| 7,648,273 B2* | 1/2010 | Manzke | ................. | A61B 6/107 250/515.1 |
| 8,057,097 B1 | 11/2011 | Tybinkowski | | |
| 8,787,522 B2* | 7/2014 | Smith | ................... | A61B 6/482 378/20 |
| 9,968,308 B2* | 5/2018 | Kawase | ................. | A61B 6/035 |
| 10,064,592 B2* | 9/2018 | Kawase | ................. | A61B 6/107 |
| 10,231,683 B2* | 3/2019 | Shimada | ............. | A61B 6/4417 |
| 11,517,271 B2* | 12/2022 | Achleitner | ........... | A61B 6/4441 |
| 11,540,789 B1* | 1/2023 | Boone | ................. | A61B 6/4085 |
| 2009/0110152 A1 | 4/2009 | Manzke et al. | | |
| 2023/0094501 A1* | 3/2023 | Lautenschlaeger | .... | A61B 6/107 378/203 |
| 2024/0000400 A1* | 1/2024 | Giebel | ................... | A61B 6/035 |

* cited by examiner

COMPUTED TOMOGRAPHY DEVICE HAVING A RADIATION PROTECTION APPARATUS FOR COVERING AN OPENING OF A GANTRY

CROSS-REFERENCE TO RELATED APPLICATION(S)

The present application claims priority under 35 U.S.C. § 119 to German Patent Application No. 10 2021 210 677.3, filed Sep. 24, 2021, the entire contents of which are incorporated herein by reference.

FIELD

One or more example embodiments of the present invention relate to a computed tomography device (CT device).

BACKGROUND

Mobile computed tomography devices are increasingly being used in environments that were not originally designed for operating a device that emits ionizing scatter radiation. Examples of such environments include intensive care units, operating and intervention rooms, and mobile stroke units. To protect the surrounding area of the computed tomography device from scatter radiation, the paneling of the computed tomography device may have layers of a radiation protection material, such as lead. Measures are also required to protect the surrounding area of the computed tomography device from scatter radiation emitted from an opening of the computed tomography device at a front side or rear side of a gantry of the computed tomography device.

U.S. Pat. No. 8,057,097 B1 discloses a radiation-protective curtain pivotably connected to a scanner so as to cover at least one side of the opening in the scanner during scanning.

DE 10 2020 206 784 A1 discloses a radiation protection apparatus comprising a radiation-protective curtain and a radiation protection apparatus comprising a radiation protection body for covering a tunnel-shaped opening of a gantry of a computed tomography device.

SUMMARY

An object of one or more example embodiments of the present invention is to provide improved protection of the area around a computed tomography device from a stray radiation emitted from an opening of a gantry of the computed tomography device. Each subject matter of an independent claim achieves this object. Further advantageous aspects of one or more example embodiments of the present invention are set forth in the dependent claims.

One or more example embodiments of the present invention relate to a computed tomography device having a gantry having an opening and a radiation protection apparatus for covering the opening, wherein the radiation protection apparatus has a radiation protection cover and a pivoting apparatus, wherein an object under examination can be inserted into the opening along a system axis of the gantry when the radiation protection cover is in a first position relative to the gantry, wherein the radiation protection cover is pivotably mounted relative to the gantry about a pivot axis via the pivoting apparatus such that a first pivoting motion of the radiation protection cover about the pivot axis enables the radiation protection cover to be lowered relative to the gantry from the first position to a second position.

In particular, the radiation protection cover can be of dimensionally stable design. For example, the radiation protection cover can be made of a dimensionally stable radiation protection material and/or be essentially impermeable to scatter rays of the ionizing radiation used in the computed tomography device to examine the patient. For example, the dimensionally stable radiation protection material can be lead-containing or lead-free. Alternatively or in addition, the radiation protection cover can have, for example, a dimensionally stable frame and a flexible sheet-like radiation protection material stretched over the dimensionally stable frame.

In particular, it can be provided that a vertical position of a first edge of the radiation protection cover is lower in the second position of the radiation protection cover than in the first position of the radiation protection cover. In particular, the first edge of the radiation protection cover can be located on a side of the radiation protection cover facing away from the pivot axis. The pivot axis can be located, for example, in a region of a second edge of the radiation protection cover.

The pivot axis can, for example, be essentially perpendicular to the system axis, in particular can be perpendicular to the system axis. The pivot axis can, for example, be essentially parallel to the system axis, in particular can be parallel to the system axis. The pivot axis can, for example, be skewed with respect to the system axis, and in particular neither essentially perpendicular nor essentially parallel to the system axis.

The opening can, for example, be tunnel-shaped and/or extend along the system axis. The system axis can, for example, pass through the opening, in particular through a central region of the opening. The system axis can, for example, pass through an isocenter of the computed tomography device. In particular, it can be provided that the vertical position of the first edge of the radiation protection cover is higher than a vertical position of the system axis both in the first position of the radiation protection cover and in the second position of the radiation protection cover.

In particular, the pivoting apparatus can be a pivot bearing and/or can be in the form of a folding mechanism. The radiation protection apparatus is designed such that when the radiation protection cover is in the first position relative to the gantry, a patient can be positioned relative to the gantry such that the head of the patient is in the opening, and such that when the radiation protection cover is in the second position relative to the gantry, the radiation protection cover does not come into contact with the patient.

Such a radiation protection apparatus is easily accessible from both edge areas to the left and right of the patient bed where the operating personnel are located for the examination and/or to prepare for the examination, in particular both for lowering the radiation protection cover from the first position and for raising the radiation protection cover from the second position.

One embodiment provides that the radiation protection apparatus furthermore has a locking system, wherein the locking system is designed to lock the radiation protection cover in the first position relative to the gantry and to lock the radiation protection cover in the second position relative to the gantry.

The locking system can in particular be designed to secure the radiation protection cover in a form-fit and/or force-fit manner against lowering and/or against lifting when the radiation protection cover is in the first position. In particular, the locking system can be designed to secure the radiation protection cover in a form-fit and/or force-fit manner against lowering and/or lifting when the radiation protection cover is in the second position.

In addition, it can be provided that the locking system is designed to lock the radiation protection cover in a third position relative to the gantry. For example, it can be provided that the third position is located between the first position and the second position, that the first position is located between the third position and the second position, or that the second position is located between the first position and the third position. In particular, it can be provided that the locking system is of stepless design and/or is designed to lock the radiation protection cover in any position relative to the gantry that the radiation protection cover can occupy while pivoting about the pivot axis.

One embodiment provides that the radiation protection apparatus additionally has a damper for braking the first pivoting motion of the radiation protection cover. The damper can be a rotational damper and/or a torsion spring, for example.

In addition, it can be provided that the radiation protection cover is pivotably mounted relative to the gantry about the pivot axis via the pivoting apparatus such that a second pivoting motion of the radiation protection cover about the pivot axis enables the radiation protection cover to be raised relative to the gantry from the second position to the first position.

In addition, it can be provided that the radiation protection apparatus furthermore has a pivot drive for driving the first pivoting motion and/or for driving the second pivoting motion. For example, the pivot drive can be designed to exert a torque on the radiation protection cover with respect to the pivot axis, which pivots the radiation protection cover to the second position.

One embodiment provides that the gantry has an inner region and paneling for separating the inner region from the external environment, wherein the radiation protection cover abuts a region of the paneling when the radiation protection cover is in the first position of the radiation protection cover, wherein the radiation protection cover extends away from the region of the paneling when the radiation protection cover is in the second position of the radiation protection cover.

One embodiment provides that the radiation protection cover extends flatly in the cover plane, and the cover plane is essentially parallel to the pivot axis. For example, an angle between the cover plane and the system axis can be greater than 30 degrees and/or less than 60 degrees, in particular approximately 45 degrees, when the radiation protection cover is in the second position of the radiation protection cover. Another embodiment provides that the radiation protection cover extends flatly in the cover plane and that the cover plane and the pivot axis intersect at an angle that is significantly non-zero, for example approximately 45 degrees.

The pivot axis can be located, for example, in a region of a second edge of the radiation protection cover. The first edge of the radiation protection cover and the second edge of the radiation protection cover can, in particular, be disposed opposite one another with respect to a central region of the radiation protection cover. The distance between the first edge of the radiation protection cover and the pivot axis can be for example greater than 10 cm, in particular greater than 20 cm, in particular greater than 30 cm. The distance between the first edge of the radiation protection cover and a second edge of the radiation protection cover can be for example greater than 10 cm, in particular greater than 20 cm, in particular greater than 30 cm.

In addition, it can be provided that the radiation protection cover can be lowered further beyond the second position, for example such that the radiation protection cover can assume a position relative to the gantry in which the plane of the cover is essentially perpendicular, in particular perpendicular, to the system axis and/or in which the radiation protection cover abuts an edge of the opening. This can be useful, for example, for a calibration measurement in which an object under examination in the form of a phantom can be disposed in the opening without parts connected to the object under examination protruding from the opening.

One embodiment provides that the system axis is essentially horizontal, in particular horizontal, and that the pivot axis is essentially horizontal, in particular horizontal. One embodiment provides that the pivot axis is located above the opening.

In particular, it can be provided that the vertical position of the first edge of the radiation protection cover in the first position of the radiation protection cover is higher than a vertical position of the pivot axis and/or that the vertical position of the first edge of the radiation protection cover in the second position of the radiation protection cover is lower than a vertical position of the pivot axis.

In one embodiment, the radiation protection cover has a region that is transparent to visible light such that the object under examination is visible through the radiation protection cover when the object under examination is in the opening and when the radiation protection cover is in the second position of the radiation protection cover.

This allows better patient observation and, due to the incoming light, enables patient well-being to be improved. In addition, it allows sufficient light to enter the opening even if the rear side of the opening is closed off by a radiation protective body that is opaque to visible light. In particular, the radiation protection cover can be made of a radiation protection material that is transparent to visible light. For example, the radiation protection cover can be made of lead glass or have a lead glass window.

One embodiment provides that the radiation protection apparatus furthermore has a radiation protection curtain, wherein the radiation protection curtain is attached to the radiation protection cover and hangs down from the radiation protection cover.

The radiation protection curtain enables gaps between the paneling of the gantry on the one hand and the patient and/or patient bed on the other hand to be covered, for example. In particular, the radiation protection curtain can be made of a flexible sheet-like radiation protection material and/or be essentially impermeable to scatter rays of the ionizing radiation used in the computed tomography device for examining the object under examination. The flexible sheet-like radiation protection material can, for example, be lead-free or lead-containing. For example, the radiation protection curtain can have a region transparent to visible light, for example in the form of a lead glass window.

One embodiment provides that a first lateral portion of the radiation protection curtain extends from the gantry to a first edge of the radiation protection cover, in particular extends essentially parallel to the system axis, and a second lateral portion of the radiation protection curtain extends from the gantry to the first edge of the radiation protection cover, in particular extends essentially parallel to the system axis.

It can also be provided that a front portion of the radiation protection curtain extends from the first lateral portion of the radiation protection curtain to the second lateral portion of the radiation protection curtain, in particular extends essentially perpendicular to the system axis. In addition, it can be provided that the system axis is located between the first lateral portion of the radiation protection curtain and the second lateral portion of the radiation protection curtain when the radiation protection cover is in the second position of the radiation protection cover.

Lowering and raising the radiation protection cover causes the radiation protection curtain to be moved essentially vertically relative to the patient. This reduces the risk of cables and/or tubes connected to the patient being entrained and damaged by the radiation protection curtain. By being attached to the radiation protection cover, the radiation protection curtain can be positioned relative to the patient in such a way that as little weight as possible of the radiation protection curtain is borne by the patient and that the weight of the radiation protection curtain borne by the patient is distributed as evenly as possible over the affected areas of the patient.

One embodiment provides that the gantry has a first gantry part and a second gantry part, wherein the first gantry part has a rotatably mounted rotor having a projection data acquisition system, wherein the second gantry part has at least one section of the opening, wherein the radiation protection cover is connected to the second gantry part via the pivoting apparatus and is pivotably mounted relative to the second gantry part about the pivot axis. The projection data acquisition system can have, for example, an X-ray source and an X-ray detector operating in conjunction with the X-ray source.

The first gantry part can be movably mounted relative to the second gantry part such that a translational movement of the first gantry part relative to the second gantry part can be executed while, at the same time, the second gantry part is stationary relative to the object under examination and the radiation protection apparatus is stationary relative to the object under examination and relative to the at least one section of the opening when the object under examination is located in the opening.

The object under examination can be, for example, a body part of a patient, in particular a head of a patient. The computed tomography device can be in particular a head computed tomography device and/or a mobile computed tomography device.

The patient can be, for example, a human being, in particular a baby, or an animal. A longitudinal axis of the patient can be, for example, parallel, in particular identical, to the system axis, or skewed, or intersect the system axis.

The object under examination can be, for example, a subject, in particular a phantom for calibrating the computed tomography device.

In one embodiment, the first gantry part has a pivot bearing and a supporting structure, wherein the rotor is connected to the supporting structure via the pivot bearing and is rotatably mounted relative to the supporting structure about the system axis.

The computed tomography device can also have, for example, a lighting system designed to illuminate the opening at least when the radiation protection cover is in the second position of the radiation protection cover.

The lighting system can have, for example, a gantry-side light source which is attached to the gantry in the region of the opening. Gantry-side light sources can be attached, for example, to the first gantry part and/or the second gantry part in each case. In addition, a gantry-side light source can be provided that is attached to the rotor and illuminates the opening through a transparent region of the gantry paneling.

The lighting system can have, for example, a cover-side light source attached to the radiation protection cover such that the light source illuminates the opening when the radiation protection cover is in the second position relative to the gantry. The lighting system can have, for example, a rear light source attached to a radiation protection body closing off the rear side of the opening.

The lighting system can be used to provide sufficient illumination of the opening even when the rear side of the opening is closed off by a radiation protection body that is opaque to visible light.

The computed tomography device can also have, for example, a camera system designed to optically capture the object under examination at least when the object under examination is located in the opening and when the radiation protection cover is in the second position of the radiation protection cover.

The use of the camera system within the radiation protection area, for example inside the opening, enables a patient to be observed even when visible light cannot penetrate outward from the opening or when a patient cannot be observed through an area of the radiation protection cover that is transparent to visible light. In particular, the computed tomography device can have a display. For example, an image of the object under examination produced by the camera system can be shown on the display.

The camera system can have, for example, a camera attached to the gantry and/or a camera attached to the radiation protection cover and/or a camera attached to a radiation protection body which closes off the rear side of the opening. In particular, the camera attached to the gantry can be attached to a portion of the gantry paneling that delimits the opening. In addition, it can be provided that the camera system has at least one camera light source, thereby forming the lighting system. For example, the camera light source can have a ring of light emitting diodes annularly surrounding the camera lens.

The computed tomography device can also have, for example, an acoustic system designed to transmit an acoustic signal to the object under examination and/or receive an acoustic signal emanating from the object under examination at least when the object under examination is in the opening and when the radiation protection cover is in the second position of the radiation protection cover.

The acoustic system can have, for example, a microphone and/or a speaker. The microphone can be attached, for example, to the gantry or to the radiation protection cover or to a radiation protection body that closes off the rear side of the opening. The speaker can be attached, for example, to the gantry or to the radiation protection cover or to a radiation protection body that closes off the rear side of the opening.

The computed tomography device can furthermore have, for example, an optical system designed to transmit an optical signal to the object under examination at least when the object under examination is in the opening and when the radiation protection cover is in the second position of the radiation protection cover.

The optical system can have, for example, a display for displaying optical signals in the form of text and/or images and/or a projector for projecting optical signals in the form of light beams, particularly laser beams. The display can be attached, for example, to the gantry or to the radiation protection cover or to a radiation protection body that closes off the rear side of the opening. The projector can be attached, for example, to the gantry or to the radiation protection cover or to a radiation protection body that closes off the rear side of the opening.

In addition, the computed tomography device can have a radiation protection body that can be detachably connected to the gantry such that it covers a rear side of the opening. In particular, the rear side of the opening can be located at the rear side of the gantry, wherein a front side of the gantry faces the radiation protection apparatus. In particular, it can be provided that the first gantry part has the rear side of the opening and that the second gantry part has the front side of the opening. The radiation protection device can have, for example, a power supply interface and/or a data transmission interface for at least one component of the lighting system, the camera system, the acoustic system and/or the optical system.

The power supply interface can be, for example, contactless or contact-based and/or designed for power transfer from the gantry to the at least one component. The data transmission interface can be for example contactless or contact-based and/or designed for data transmission from the gantry to the at least one component and/or from the at least one component to the gantry.

Within the scope of the present invention, features described with respect to different embodiments of the present invention and/or different categories of claims (method, use, apparatus, system, arrangement, etc.) may be combined to form further embodiments of the present invention. For example, a claim relating to an apparatus may also be further developed using features described or claimed in connection with a method, and vice versa. Functional features of a method can be executed by correspondingly implemented physical components. The use of the indefinite articles "a" or "an" does not exclude the possibility that the feature concerned may be present more than once.

BRIEF DESCRIPTION OF THE DRAWINGS

The present invention will now be explained using exemplary embodiments and with reference to the accompanying figures. The representation in the figures is schematic, greatly simplified and not necessarily to scale.

DETAILED DESCRIPTION

Figure 1:
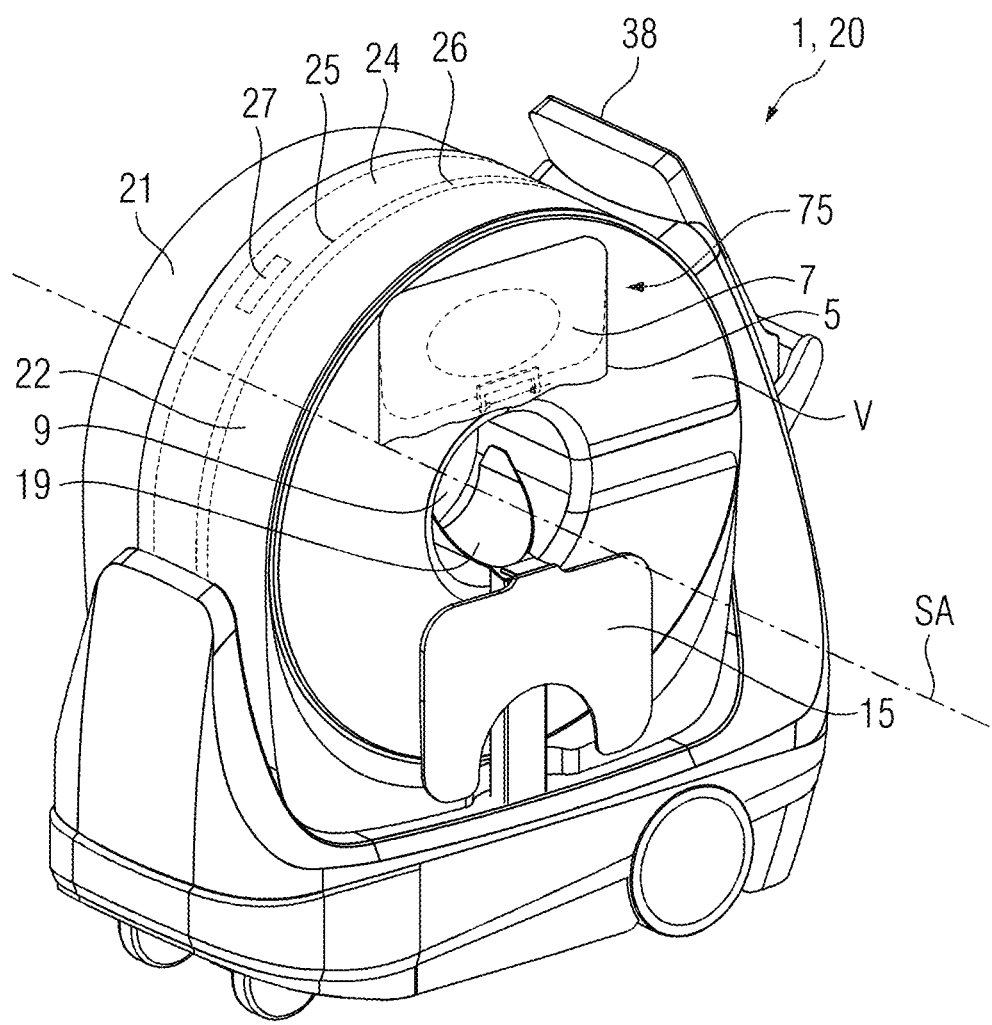
FIG. 1 shows a computed tomography device having a radiation protection apparatus for covering an opening.

FIG. 1 shows a computed tomography device 1, having a gantry 20 with an opening 9, and a radiation protection apparatus 75 for covering the opening 9, wherein the radiation protection apparatus 75 has a radiation protection cover 7 and a pivoting apparatus 70, wherein an object under examination 14 can be inserted into the opening 9 along a system axis SA of the gantry 20 when the radiation protection cover 7 is in a first position relative to the gantry 20, wherein the radiation protection cover 7 is pivotably mounted relative to the gantry 20 about a pivot axis 7A via the pivoting apparatus 70 such that a first pivoting motion of the radiation protection cover 7 about the pivot axis 7A enables the radiation protection cover 7 to be lowered relative to the gantry 20 from the first position to a second position.

The pivot axis 7A is located in a region of a second edge 72 of the radiation protection cover 7. The first edge 71 and the second edge 72 are disposed opposite one another with respect to a central region of the radiation protection cover 7.

The object under examination 14 is the head of the patient 13. The computed tomography device 1 is a mobile head computed tomography device. The computed tomography device 1 furthermore has a head tray 19 in which the head of the patient 13 can be accommodated, and an upper body support plate 15 on which the upper body of the patient 13 can be supported.

The gantry 20 has a first gantry part 21 and a second gantry part 22, wherein the first gantry part 21 has a rotatably mounted rotor 24 having a projection data acquisition system 27, wherein the second gantry part 22 has at least one section of the opening 9, wherein the radiation protection cover 7 is connected to the second gantry part 22 via the pivoting apparatus 70 and is pivotably mounted relative to the second gantry part 22 about the pivot axis 7A.

The first gantry part 21 is movably mounted relative to the second gantry part 22 such that a translational movement of the first gantry part 21 relative to the second gantry part 22 can be performed while, at the same time, the second gantry part 22 is stationary relative to the object under examination 14 and the radiation protection apparatus 75 is stationary relative to the object under examination 14 and relative to the at least one section of the opening 9 when the object under examination 14 is located in the opening 9.

The first gantry part 21 has a rotational mount 25 and a supporting structure 26, wherein the rotatably mounted rotor 24 is connected to the supporting structure 26 via the rotational mount 25 and is rotatably mounted relative to the supporting structure 26 about the system axis SA.

Figure 2:
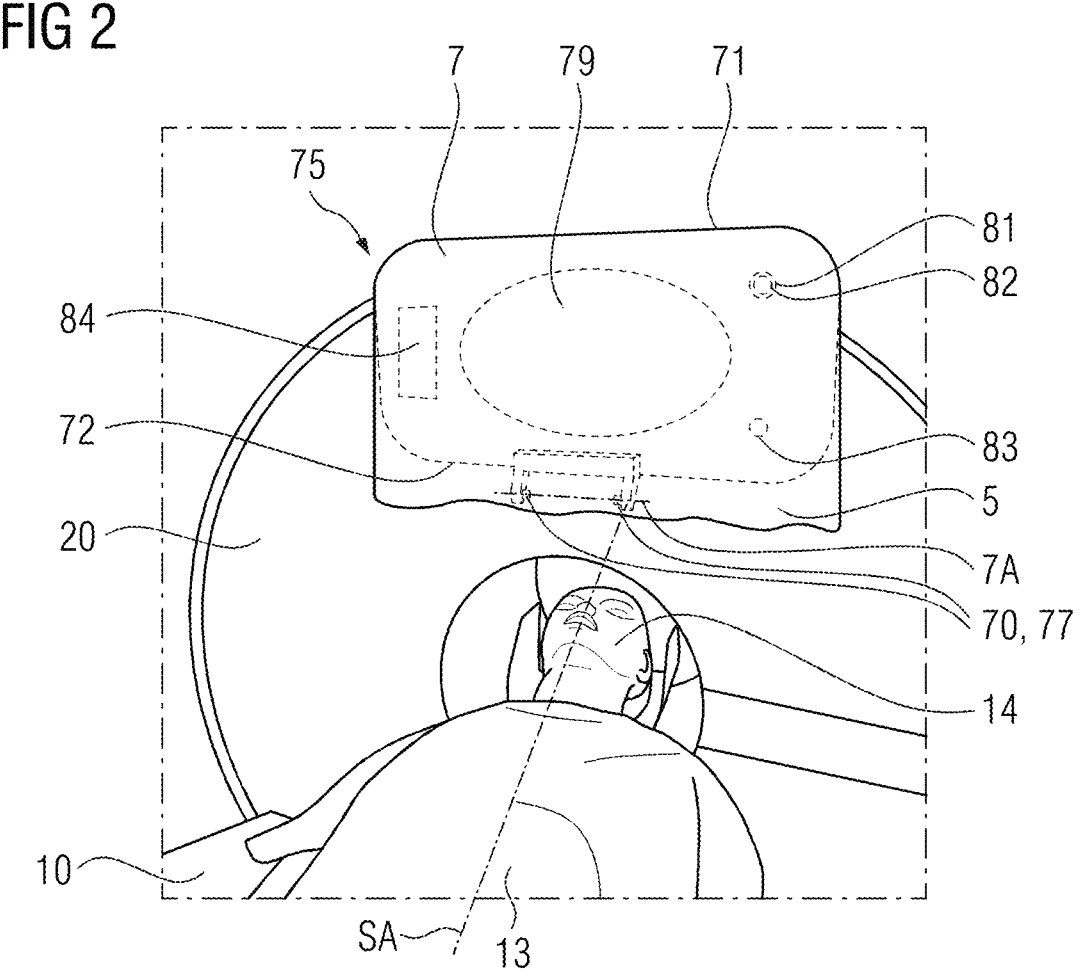
FIG. 2 shows the computed tomography device, wherein the radiation protection cover is in the first position.

FIG. 2 shows the computed tomography device 1, wherein the radiation protection cover 7 is in the first position. The radiation protection apparatus 75 furthermore has a damper 77 for braking the first pivoting motion of the radiation protection cover 7.

The computed tomography device 1 furthermore has a lighting system 81 designed to illuminate the opening 9 at least when the radiation protection cover 7 is in the second position of the radiation protection cover 7. The lighting system 81 of the computed tomography device 1 shown in FIG. 2 has a camera light source attached to the radiation protection cover 7.

The computed tomography device 1 also has a camera system 82 designed to optically capture the object under examination 14 at least when the object under examination 14 is located in the opening 9 and when the radiation protection cover 7 is in the second position of the radiation protection cover 7. The camera system 82 of the computed tomography device 1 shown in FIG. 2 has a camera attached to the radiation protection cover 7. The computed tomography device 1 has the display screen 38. For example, an image of the object under examination 14 generated by the camera system 82 can be displayed on the screen 38.

The computed tomography device 1 also has an acoustic system 83 designed to transmit an acoustic signal to the object under examination 14 and/or to receive an acoustic signal from the object under examination 14 at least when the object under examination 14 is located in the opening 9 and when the radiation protection cover 7 is in the second position of the radiation protection cover 7. The acoustic system 83 of the computed tomography device 1 shown in FIG. 2 has a microphone and a speaker attached to the radiation protection cover 7.

The computed tomography device 1 furthermore has an optical system 84 which is designed to transmit an optical signal to the object under examination 14 at least when the object under examination 14 is positioned in the opening 9 and when the radiation protection cover 7 is in the second position of the radiation protection cover 7. The optical system 84 of the computed tomography device 1 shown in FIG. 2 has a display attached to the radiation protection cover 7.

Figure 3:
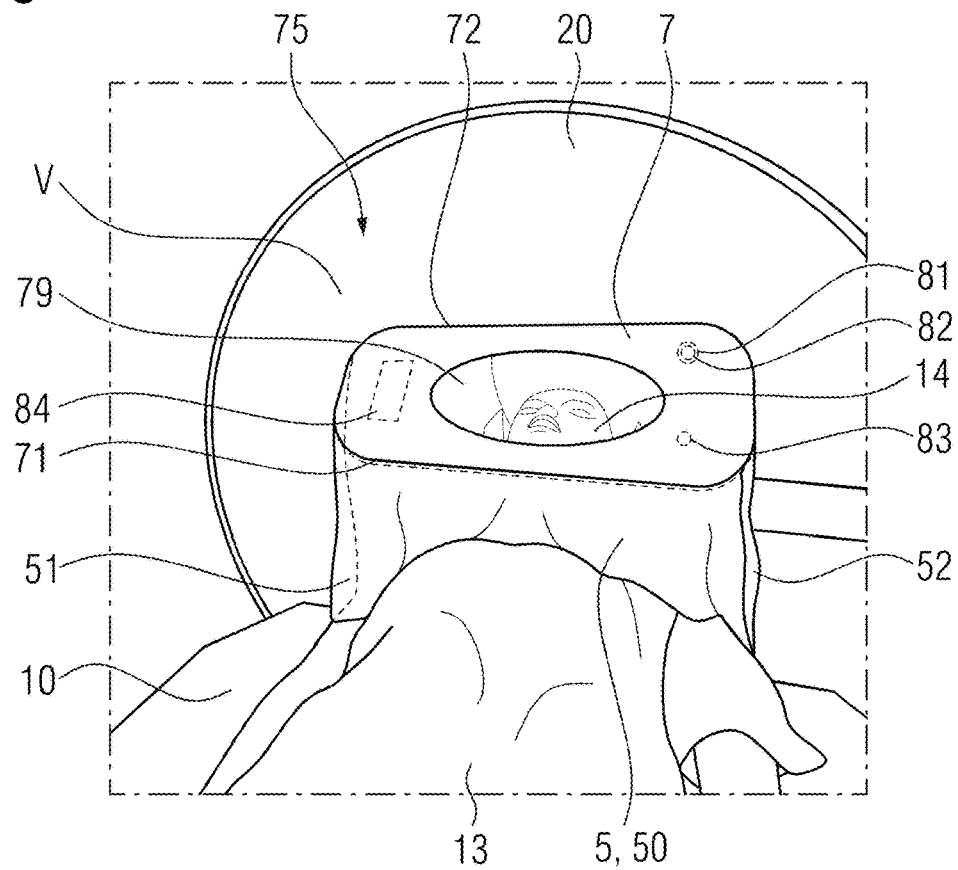
FIG. 3 shows the computed tomography device, wherein the radiation protection cover is in the second position.

FIG. 3 shows the computed tomography device 1, wherein the radiation protection cover 7 is in the second position. The radiation protection cover 7 has a region 79 transparent to visible light, such that the object under examination 14 is visible through the radiation protection cover 7 when the object under examination 14 is located in the opening 9 and when the radiation protection cover 7 is in the second position of the radiation protection cover 7.

The radiation protection apparatus 75 also has a radiation protection curtain 5, wherein the radiation protection curtain 5 is attached to the radiation protection cover 7 and hangs down from the radiation protection cover 7. A first lateral portion 51 of the radiation protection curtain 5 extends from the gantry 20 to a first edge 71 of the radiation protection cover 7. A second lateral portion 52 of the radiation protection curtain 5 extends from the gantry 20 to the first edge 71 of the radiation protection cover 7. A front portion 50 of the radiation protection curtain 5 extends from the first lateral portion 51 of the radiation protection curtain 5 to the second lateral portion 52 of the radiation protection curtain 5. The system axis SA is located between the first lateral portion 51 of the radiation protection curtain 5 and the second lateral portion 52 of the radiation protection curtain 5 when the radiation protection cover 7 is in the second position of the radiation protection cover 7.

Figure 4:
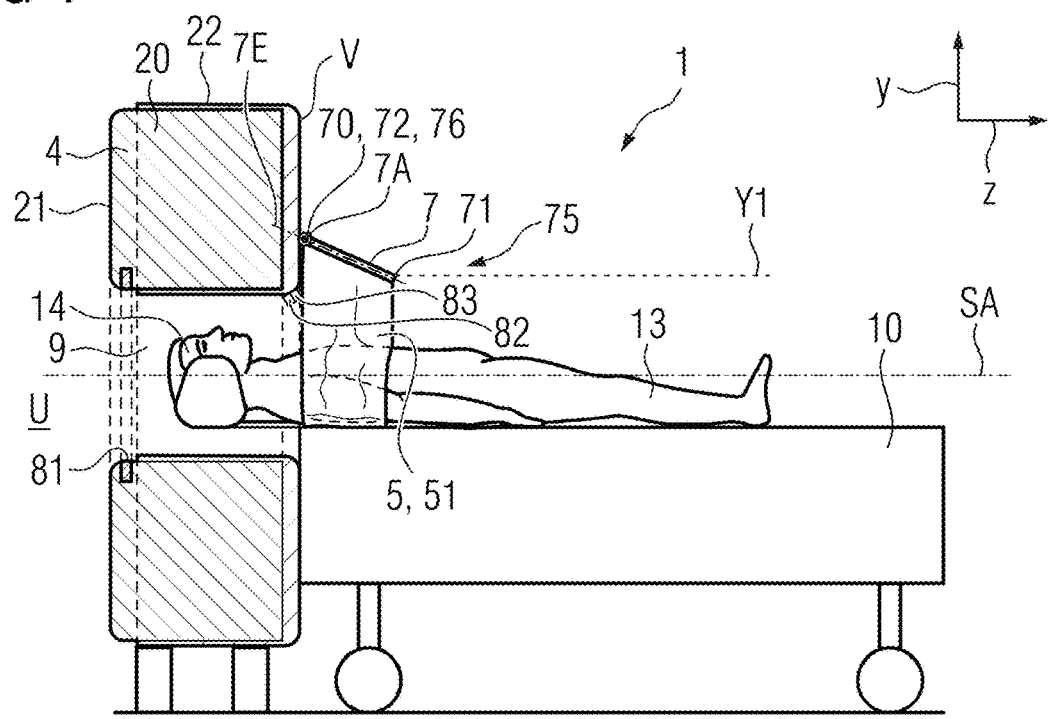
FIG. 4 shows the computed tomography device with a patient bed.

FIG. 4 shows the computed tomography device 1 with a patient bed 10 for accommodating the patient 13. The gantry 20 has an interior region 4 and paneling V (also referred to as a covering V) for separating the interior region 4 from the external environment U, wherein the radiation protection cover 7 abuts a region of the paneling V when the radiation protection cover 7 is in the first position of the radiation protection cover 7, wherein the radiation protection cover 7 projects away from the region of the paneling V when the radiation protection cover 7 is in the second position of the radiation protection cover 7.

The radiation protection cover 7 extends flatly in a cover plane 7E, wherein the cover plane 7E is essentially parallel to the pivot axis 7A. The system axis SA is horizontal and parallel to the horizontal direction z. The pivot axis 7A is horizontal and perpendicular to the horizontal direction z. The pivot axis 7A is located above the opening 9.

The vertical position Y1 of the first edge 71 of the radiation protection cover 7 in the second position of the radiation protection cover 7 is lower than in the first position of the radiation protection cover 7. With respect to the vertical direction y, there is a space between the patient 13 and the radiation protection cover 7. The risk of the patient 13 colliding with the radiation protection cover 7 is thereby reduced.

The radiation protection apparatus 75 also has a locking system 76, wherein the locking system 76 is designed to lock the radiation protection cover 7 in the first position relative to the gantry 20 and to lock the radiation protection cover 7 in the second position relative to the gantry 20.

The head of the patient 13 can be inserted into the opening 9 along the system axis SA even if the longitudinal axis of the patient 13 is not parallel to the system axis SA. This may be necessary, for example, in the case of spinal anomalies.

The camera system 82 of the computed tomography device 1 shown in FIG. 4 has a camera attached to the gantry 20 in a region of the front side of the opening 9. The acoustic system 83 of the computed tomography device 1 shown in FIG. 4 has a microphone and a speaker attached to the gantry 20 in a region of the front side of the opening 9.

The lighting system 81 of the computed tomography device 1 shown in FIG. 4 has a gantry-side light source which is attached to the first gantry part 21, in particular to paneling of the first gantry part 21, in a region of the rear side of the opening 9 and is in the form of a light ring. The patient 13 is thus not dazzled by light emanating from the light ring.

The light ring is disposed coaxially with respect to the system axis SA. The arrangement of the light ring on the first gantry part 21 and the dimensions of the paneling of the second gantry part 22 in the region of the opening 9 are adjusted to one another such that the paneling of the second gantry part 22 in the region of the opening 9 does not conceal the light ring even when the first gantry part 21 is fully retracted into the second gantry part 22. Alternatively or additionally, it can be provided that a gantry-side light source, in particular in the form of a light ring disposed coaxially with respect to the system axis SA, is attached to the second gantry part 22 in the region of the opening 9.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of the embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing embodiments. The present invention may, however, be embodied in many alternate forms and should not be construed as limited to only the embodiments set forth herein.

What is claimed is:

1. A computed tomography device, comprising:
   a gantry having an opening; and
   a radiation protection apparatus configured to cover the opening, the radiation protection apparatus including a radiation protection cover and a pivoting apparatus, wherein
   the opening is configured to receive an object under examination inserted along a system axis of the gantry when the radiation protection cover is in a first position relative to the gantry, and
   the radiation protection cover is pivotably mounted relative to the gantry about a pivot axis via the pivoting apparatus such that a first pivoting motion of the radiation protection cover about the pivot axis causes the radiation protection cover to be lowered relative to the gantry from the first position to a second position.

2. The computed tomography device as claimed in claim 1,
   wherein the radiation protection apparatus includes a locking system, and
   wherein the locking system is configured to lock the radiation protection cover in the first position, and to lock the radiation protection cover in the second position.

3. The computed tomography device as claimed in claim 2,
   wherein the radiation protection apparatus includes a damper configured to brake the first pivoting motion of the radiation protection cover.

4. The computed tomography device as claimed in claim 2,
   wherein the gantry includes an interior and a covering separating the interior from an external environment,
   wherein the radiation protection cover abuts a region of the covering when the radiation protection cover is in the first position, and
   wherein the radiation protection cover projects away from the region of the covering when the radiation protection cover is in the second position.

5. The computed tomography device as claimed in claim 2,
   wherein the radiation protection cover extends flatly in a cover plane, and
   wherein the cover plane is substantially parallel to the pivot axis.

6. The computed tomography device as claimed in claim 1,
   wherein the radiation protection apparatus includes a damper configured to brake the first pivoting motion of the radiation protection cover.

7. The computed tomography device as claimed in claim 1,
wherein the gantry includes an interior and a covering separating the interior from an external environment,
wherein the radiation protection cover abuts a region of the covering when the radiation protection cover is in the first position, and
wherein the radiation protection cover projects away from the region of the covering when the radiation protection cover is in the second position.

8. The computed tomography device as claimed in claim 7, wherein the radiation protection cover has a region that is transparent to visible light, such that the object under examination is visible through the radiation protection cover when the object under examination is located in the opening and when the radiation protection cover is in the second position.

9. The computed tomography device as claimed in claim 1,
wherein the radiation protection cover extends flatly in a cover plane, and
wherein the cover plane is substantially parallel to the pivot axis.

10. The computed tomography device as claimed in claim 1,
wherein the system axis is substantially horizontal and wherein the pivot axis is substantially horizontal.

11. The computed tomography device as claimed in claim 1, wherein the pivot axis is located above the opening.

12. The computed tomography device as claimed in claim 1, wherein the radiation protection cover has a region that is transparent to visible light, such that the object under examination is visible through the radiation protection cover when the object under examination is located in the opening and when the radiation protection cover is in the second position.

13. The computed tomography device as claimed in claim 1,
wherein the radiation protection apparatus includes a radiation protection curtain, and
wherein the radiation protection curtain is attached to the radiation protection cover and hangs down from the radiation protection cover.

14. The computed tomography device as claimed in claim 13,
wherein a first lateral portion of the radiation protection curtain extends from the gantry to a first edge of the radiation protection cover,
wherein a second lateral portion of the radiation protection curtain extends from the gantry to the first edge of the radiation protection cover,
wherein a front portion of the radiation protection curtain extends from the first lateral portion of the radiation protection curtain to the second lateral portion of the radiation protection curtain, and
wherein the system axis is located between the first lateral portion of the radiation protection curtain and the second lateral portion of the radiation protection curtain when the radiation protection cover is in the second position.

15. The computed tomography device as claimed in claim 1,
wherein the gantry has a first gantry part and a second gantry part,
wherein the first gantry part has a rotatably mounted rotor incorporating a projection data acquisition system,
wherein the second gantry part has at least one section of the opening,
wherein the radiation protection cover is connected to the second gantry part via the pivoting apparatus, and the radiation protection cover is pivotably mounted relative to the second gantry part about the pivot axis, and
wherein the first gantry part is movably mounted relative to the second gantry part such that the first gantry part is configured for a translational movement relative to the second gantry part, while at the same time, the second gantry part is stationary relative to the object under examination, and the radiation protection apparatus is stationary relative to the object under examination and relative to the at least one section of the opening when the object under examination is located in the opening.

16. The computed tomography device as claimed in claim 15,
wherein the first gantry part has a rotational mount and a supporting structure, and
wherein the rotatably mounted rotor is connected to the supporting structure via the rotational mount, and the rotatably mounted rotor is rotatably mounted relative to the supporting structure about the system axis.

17. The computed tomography device as claimed in claim 1, further comprising:
a lighting system configured to illuminate the opening at least when the radiation protection cover is in the second position.

18. The computed tomography device as claimed in claim 1, further comprising:
a camera system configured to optically detect the object under examination at least when the object under examination is located in the opening and when the radiation protection cover is in the second position.

19. The computed tomography device as claimed in claim 1, further comprising:
an acoustic system configured to at least one of transmit an acoustic signal to the object under examination or receive an acoustic signal from the object under examination at least when the object under examination is located in the opening and when the radiation protection cover is in the second position.

20. The computed tomography device as claimed in claim 1, further comprising:
an optical system configured to transmit an optical signal to the object under examination at least when the object under examination is located in the opening and when the radiation protection cover is in the second position.

* * * * *